United States Patent
Heimberger

[11] Patent Number: 5,888,192
[45] Date of Patent: Mar. 30, 1999

[54] CONTROL DEVICE FOR ENDOCSCOPES

[75] Inventor: Rudolf Heimberger, Oberderdingen, Germany

[73] Assignee: Richard Wolf GmbH, Knittlingen, Germany

[21] Appl. No.: 984,739

[22] Filed: Dec. 4, 1997

[30] Foreign Application Priority Data

Dec. 6, 1996 [DE] Germany .................. 196 50 721.9

[51] Int. Cl.$^6$ ................................................ A61B 1/00
[52] U.S. Cl. ............................................. 600/146; 600/148
[58] Field of Search ................................. 600/139, 144, 600/145, 146, 147, 148, 149, 150, 151; 403/358, 359, 326, 328

[56] References Cited

U.S. PATENT DOCUMENTS

| | | |
|---|---|---|
| 3,557,780 | 1/1971 | Sato . |
| 4,617,914 | 10/1986 | Ueda . |
| 5,464,007 | 11/1995 | Krauter et al. ............... 600/148 X |

FOREIGN PATENT DOCUMENTS

| | | | |
|---|---|---|---|
| 0 306 723 B1 | 10/1993 | European Pat. Off. ......... | A61B 1/00 |
| 25 57 545 | 2/1978 | Germany ................... | A61B 1/00 |
| 29 17 465 | 12/1979 | Germany ................... | G02B 23/00 |
| 39 05 455 A1 | 8/1989 | Germany ................... | A61B 1/00 |
| 39 43 726 C2 | 5/1995 | Germany ................... | A61B 1/00 |

*Primary Examiner*—Beverly M. Flanagan
*Attorney, Agent, or Firm*—Cohen, Pontani, Lieberman, Pavane

[57] ABSTRACT

A control device serves the steering of the distal end of an endoscope, this being by operating control cables running to the distal end of the endoscope by way of a handle. The control device is accomodated by a control housing at the proximal end of the endoscope and has an adjusting and braking mechanism for adjusting and fixing the distal endoscope end as well as further as a handle, a lever which is to be operable with one hand and which serves as a combined braking and control member. This lever, from a first position, can be rotated about an axis wherein it acts upon the control cables via a shaft connected to the handle as well as via an insert rotatably mounted in the housing and connected to the shaft, and in a second position together with the insert can be fixed against rotation by way of a friction fit via a brake effective between the control housing and the insert. The lever comprises a locking member which is operable by hand and which effects an axial offset of the shaft and the insert in the direction of the mentioned axis, wherein on operating the locking member in one direction, the insert can be brought into frictional engagement with a stationary braking element and by way of this the distal endoscope end is fixed in its respective position.

12 Claims, 3 Drawing Sheets

CONTROL DEVICE FOR ENDOCSCOPES

BACKGROUND OF THE INVENTION

The invention relates to a control device for steering the distal end of an endoscope by operating control cables running to the distal end of the endoscope by way of a handle, wherein the control device is accomodated by a control housing at the proximal end of the endoscope, and it comprises an adjusting and braking mechanism for adjusting and fixing the mentioned distal end and furthermore as a handle, a lever which is operable with one hand, serves as a combined braking and control member, and which from a first position can be rotated about an axis passing through the control housing and at the same time acts upon the control cables via a shaft connected to the handle and an insert rotatably mounted in the housing and connected to the shaft, and which in a second position together with the insert can be fixed against rotation by way of a friction fit via a brake effective between the control housing and the insert.

Such a control device for flexible endoscopes is known from the patent DE 37 29 131 C1. With this control device the control lever operating the insert in the control housing and thus the control cables is formed with a design such that it may be used for steering the distal end of the endoscope as well as for fixing the momentary setting. By way of lateral pivoting of the control lever the control device may be brought from a first operating position into a second operating position in which the brake is effective.

The disadvantage with this control device is the complicated handling and the relatively high technical expense in the assembly as well as in the adjustment of the individual components within the proximally located control housing.

SUMMARY OF THE INVENTION

The object of this invention lies in so forming a control device of the mentioned type for steering the distal end of an endoscope, that a one-handed operability of the adjusting lever for fixing the adjusting position is even further improved and that simultaneously a less expensive production and assembly including possible necessary adjustment work without limiting the function of adjustability of the endoscope is made possible.

According to the invention the above object is achieved with a control device of the previously mentioned type in that the lever comprises a locking member which is operable by hand and which effects an axial offset of the shaft and thus of the insert connected to it, and in that on operating the locking member in one direction the insert can be brought into frictional engagement with a stationary braking element.

As a result with the control device according to the invention there is no second axis about which the control lever must be laterally pivoted for operating the brake. For braking the control, the locking member on the lever needs only to be displaced about a small amount in order to function the brake.

By way of this, a considerable design expense which was necessary with the known control device is avoided without adversely affecting the braking effect with respect to this known control device.

It is further advantageous when the locking member is formed as a sliding member displaceable on the lever, and consists of a spring member which is displaceable perpendicular to the axial direction of the shaft and which on its displacement for operating the brake, with an oblique section projecting in the axial direction, in the direct vicinity of the shaft, slides wedge-like between the control housing and the control lever and thus effects the axial displacement of the shaft into the locking position.

It is useful for the lever to have guiding means for guiding the sliding member or the spring member, in that the lever consists of a rigid elongate body which comprises a first bent section on which the slide guiding means is provided and which in its shape is adapted to the outer contour of the control housing, and which comprises a second section which lies in a plane perpendicular to the axial direction of the shaft, so that the spring member encompassing the shaft is slidingly displaceable on the inner side of the second section of the body of the lever.

An advantageous further development of the invention consists in the fact that the control cables may be adjusted in two ways, this being on the one hand on the insert in the control housing and on the other hand by adjustment of the cable coatings surrounding the control cables in the longitudinal direction of the control cables.

BRIEF DESCRIPTION OF THE DRAWINGS

Further features of the invention are specified in the dependent claims and are hereinafter described in more detail by way of one embodiment example shown in the drawing. There are shown:

DETAILED DESCRIPTION OF THE INVENTION

Figure 1:
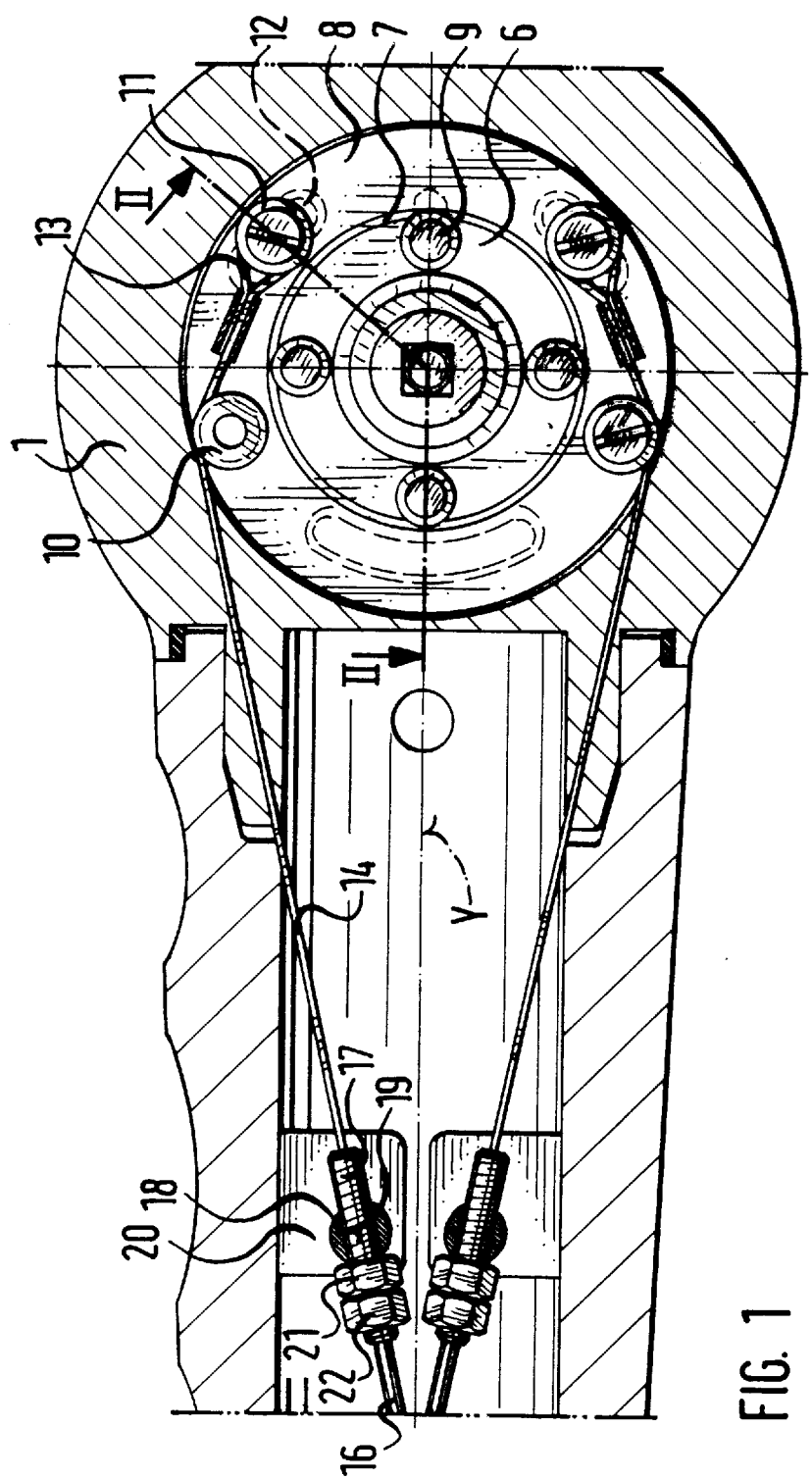
FIG. 1 a longitudinal section through a control housing located at the proximal end of an endoscope, FIG. 2a a cross section through the control housing according to FIG. 1 taken along the section line II—II, with an unoperated brake, FIG. 2b a representation corresponding to FIG. 2a with an operated brake, FIG. 3 the end, on the proximal side, of the fastening and adjusting means and FIG. 4 the setting means according to FIG. 3 serving the adjustment of a control cable, in section.
Figure 2B:
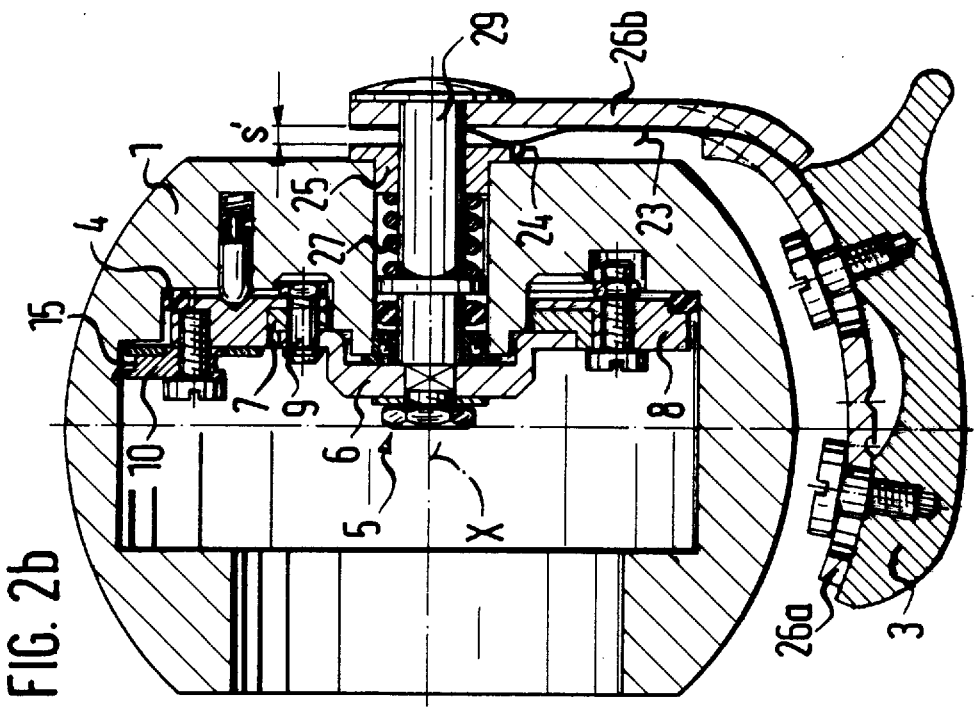
Figure 2A:
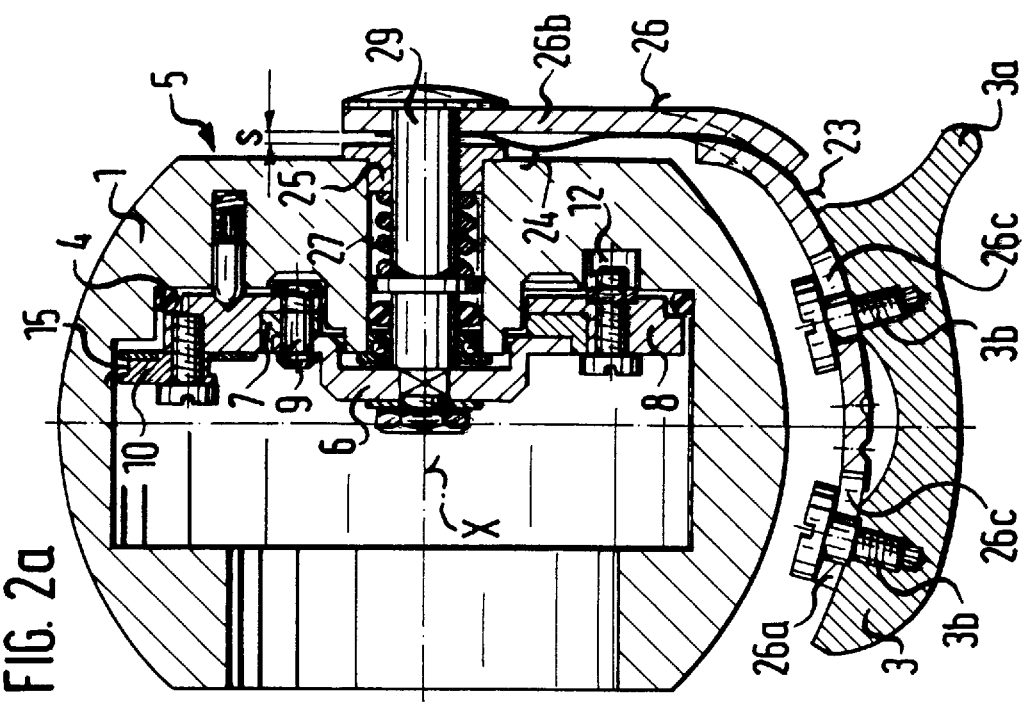

According to FIG. 1, in a control housing 1, for example with a spherical outer contour, there is mounted a disk-shaped insert which is constructed of three annular disks 6, 7 and 8 and which is mounted rotatingly about an axis and is axially displaceably mounted about a certain amount in two directions. In FIGS. 2a and 2b the axis is indicated at X, and is perpendicular to the plane of the drawing of FIG. 1. The two disks 6 and 8 consist of metal and are separated by the disk 7 of insulating material and are connected to one another by way of insulating fastening means 9. With the disk 7 and by way of the insulating fastening means 9 it is prevented that an electrical current transmission from the distal to the proximal end of the instrument is effected.

The center of the disk-shaped insert 6, 7 and 8 is interspersed by a shaft 29 lying in the direction of the axis X. The insert is rigidly fastened to the shaft 29 such that it is pivotable along with the shaft about the axis X. By way of cable eyelets 13, the control cables 14 are fastened to fastening rollers 11 which are mounted on the outer lying disk part 8. Further the outer disk part 8 carries two turning and guiding rollers 10 which turn and rotatingly mount the control cables and which prevent the cable eyelets 13 wound around the fastening rollers, when pivoting the insert 6, 7, 8 about a certain angle, from adversely affecting the adjustment of the distally deflectable endoscope end due to sliding friction on these rollers.

The turning and guiding rollers 10 are preferably adjustable in the radial direction. This offers the advantage that the distance between the control cables 14, or between the turning and guiding rollers 10 and the control housing 1 may be as small as possible, so that the control cables 14 may not come off the respective turning and guiding roller 10. In FIGS. 2a and 2b it is further shown that the cylindrical rollers 10 are equipped with a circumferential annular groove 15 as a cable guide.

The position of the fastening rollers 11 on the outer disk part 8 can also be varied in elongate formed recesses 12 or in several individual holes arranged at a distance to one another. As a rule the latter is also possible in spite of the lengthening or shortening of the control cables 14 in steps only.

Figure 3:
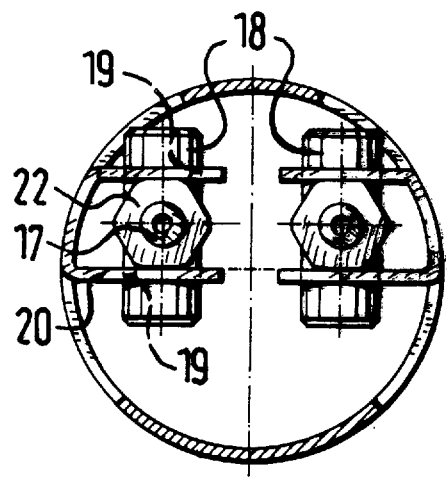
Figure 4:
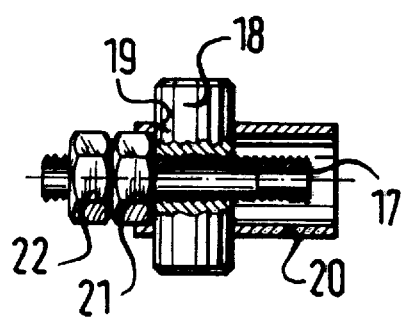

Furthermore by way of the FIGS. 1, 3 and 4 the receiver of the cable coating 16 through which the control cables pass is explained, this receiver being situated distally of the control housing 1. Since on pivoting the insert 6, 7, 8, the angle of the cable sections located between the insert and the coating receiver also changes with respect to the logitudinal axis of the instrument indicated at Y, the receivers of the proximal ends of the control cable coatings 16 are pivotingly mounted.

The cable coatings 16 according to FIGS. 3 and 4 are in each case fastened in a movable threaded sleeve 17, a cylinder 18 pivotingly mounted on U-shaped brackets 20. The cylinders 18 themselves are loosely inserted into corresponding holes 19 in the U-shaped brackets 20 so that a free floating pivoting movement is possible.

For adjusting the control cables 14 and their cable coatings 16, apart from the longitudinal setting at the fastening rollers 11, the threaded sleeves 17 may also be axially adjustable. One or both threaded sleeves 17 are firstly screwed into or out of the cylinder 18 about the required measure of length compensation by way of the nut 21. Then with the locknut 22, subsequent to setting the length, the nut 21 may be secured.

The braking effect occurs as soon as the outer disk part 8 comes into frictional engagement with a braking element which is formed here as a braking ring 4 (FIG. 2), which may be a simple O-ring. The operation of the brake with a locking member is effected according to the invention in that a handle part 3 provided on a rigid elongate lever member 26 clutches on a gripping element 3a and is displaced laterally in the logitudinal direction of the elongate lever body 26, out of the position shown in FIG. 2a, with the effect that a locking and sliding member which is connected to the handle part 3 and formed as a spring member 23 or leaf spring, with an oblique spring section 24 projecting parallel to the axis X, engages between a bearing member 25 fixed on the control housing 1, and the lever body 26, as is shown in FIG. 2b. By way of this the shaft 29 is axially displaced by a certain amount s'-s and also the outer disk part 8 is pressed against braking ring 4 which deforms at the same time, by which means the whole disk-shaped insert 6, 7, 8 of the lever body 26 rigidly connected to the shaft 29 and the distal endoscope end, is braked or fixed against further adjustment.

If one displaces the handle part 3 into its original position shown in FIG. 2a, the projecting spring section 24 reaches out of the previously expanded gap between the bearing part 25 and the section 26b of the lever body 26 lying opposite this. Simultaneously the disk-shaped insert 6, 7 and 8, by way the force exerted on it by a compression spring 27 provided on the shaft 29, is displaced back to its original position in which then again the unbraked control of the distal endoscope end with the control device 5 at the lever or the handle 3 is possible.

The lever body 26 consists of two sections, that is a bent first section 26a on which the handle 3 connected to the spring member 23 is longitudinally displaceable and which runs roughly circularly arcuate so that it is adapted to the spherical outer contour of the control housing 1, as well as an essentially straight second section 26b which lies in a plane perpendicular to the axis X. The locking or spring member 23 connected to the handle 3 is guided in the first section 26a on the outer side of the lever body 26, i.e. on the side on which the handle 3 is located, and in a second section 26b of the lever body 26 on the inner side thereof. In this way it is achieved that the spring member 23 may be very thin and is covered at nearly all locations so that it may not be inadvertently bent.

The first section 26a of the lever body 26 comprises means for guiding the longitudinally displaceable handle 3 and the spring member 23 on the lever body 26. This guiding means on the one hand may consist of longitudinal slits 26c in the lever body and screw bolts 3b which are guided in these longitudinal slits and which are so screwed with the handle 3 that there remains some play for the easy longitudinal displaceabilty of the handle 3 with the spring member 23. On the other hand further guiding means in the form of an elongate passage in the lever body is realized, the lever body guiding the spring member to the inner side of the lever.

In the braked or locked condition in which the outer disk part 8 presses against the braking ring 4, there still remains a slight distance between the control housing 1 and the disk parts 6, 7 and 8 which is necessary if the deflectional movement of the distal endoscope end is also to be possible in the braked condition in order to avoid damage to the instrument by any overloading.

In the preferred embodiment form as is shown in FIGS. 2a and 2b, the locking member is designed as a combination of the handle part 3 with the spring member 23 longitudinally displaceable on the lever 26, the spring member with its displacement in the locking or braking direction and with the oblique spring section 24, causing an axial displacement of the shaft 29 in the direction of the axis X, toward the right corresponding to FIG. 2b and thus causing the braking effect. It is also possible that the axial displacement of the shaft 29 and thus the locking and braking function may be achieved also with other suitable means, e.g. in that between the section of the lever 26 near to the axis and the bearing part 25 there is provided an annular spring member which has a thickened or oblique section which on turning this spring disk displaces the shaft 29 and the disk shaped insert 6, 7, 8 in the direction of braking or locking.

I claim:

1. An apparatus for controlling an endoscope having a longitudinal central endoscope axis, a proximal end, a distal end, and a handle, via control cables connected through the handle to the distal end, the apparatus comprising:

a control housing, positioned at the proximal end of the endoscope, having a central axis therethrough perpendicular to the endoscope, and an inner wall; and a control device, disposed at least partially within said control housing, for adjusting and fixing the distal end, comprising:

a shaft rotably mounted within said control housing, said shaft being movable a predetermined offset distance along said central axis between a first shaft position where said shaft is rotatable, and a second shaft position;

an insert, mounted on said shaft within said control housing, for attaching and guiding the control cables, a stationary braking element disposed within said control housing between said insert and said inner rear wall, for frictionally engaging said insert when said shaft is axially displaced into said second shaft position thereby at least limiting movement of the distal end, and a control member, disposed outside said control housing, having a lever connected to said shaft for imparting rotational movement to said shaft and a locking member, said control member being movable between a first and a second position, wherein in said first position said lever is rotatable about said central axis, such that selective rotary movement of said lever causes said shaft to rotate said insert and thereby steer the distal end via the control cables, and wherein in said second position, selective operation of said locking member causes said shaft to be axially displaced into said second shaft position and causes said insert to engage said braking element, thereby braking the distal end and at least limiting movement thereof.

2. The apparatus of claim 1, wherein said locking member is movably disposed on said lever, and wherein said locking member comprises an oblique section substantially near said shaft, said oblique section projecting perpendicular to direction of displacement of said shaft, such that when said oblique section is radially adjusted by movement of said locking member, said shaft is displaced for said predetermined offset distance along said central axis into one of said first and said second shaft position.

3. The apparatus of claim 2, wherein said locking member and said oblique section are elastically deformable.

4. The apparatus of claim 3, wherein said lever further comprises:

a rigid lever body; and first guiding means for slidably guiding movement of said locking member on said lever.

5. The apparatus of claim 4, further comprising a sliding handle, connected to said locking member, wherein said lever further comprises second guiding means, and wherein said sliding handle is longitudinally displaceable on said lever along said second guiding means.

6. The apparatus of claim 5, wherein said control housing comprises an outer contour, and wherein said lever further comprises:

a first section, having said first and second guiding means disposed thereon, said first section being shaped corresponding to said outer contour; and a second section disposed perpendicular to said central axis, wherein said shaft is rotationally and slidably affixed to said second section.

7. The apparatus of claim 6, wherein said insert comprises a disk mounted on said shaft, and axially displaceable for said predetermined offset distance along with said shaft when said shaft is moved along said central axis between said first and said second shaft positions.

8. The apparatus of claim 7, wherein said disk comprises:

an inner annular disk part for contact with said breaking means;

an outer annular disk part for connecting and guiding the control cables;

a middle annular disk part, composed of an insulating material positioned between said outer disk part and said inner disk part, for insulating said outer disk part from said inner disk part; and insulated fastening means for interconnecting said inner, outer, and middle disk parts in an insulated manner.

9. The apparatus of claim 8, wherein each of the control cables comprise a cable end, further comprising:

a pair of fastening rollers, positioned on said outer disk part and perpendicular thereto, each for receiving and fastening one control cable end; and a pair of turning and guiding rollers, rotably mounted on said outer disk part perpendicular thereto and at a predetermined distance from said pair of fastening rollers, for engaging portions of the control cables substantially close to said control cable ends that are each fastened to one of said fastening rollers, such that when said insert is rotated, said pair of turning and guiding rollers turn and guide the control cables, thereby steering said distal end.

10. The apparatus of claim 9, wherein said outer disk part comprises a pair of elongate recesses, each for receiving one of said fastening rollers, wherein each said fastening roller is movable along its respective elongate recess to adjust said predetermined distance to said pair of guiding and turning rollers.

11. The apparatus of claim 10, wherein said endoscope comprises a hollow tubular portion at its proximal end to said control housing, further comprising:

a cable coating for each of the control cables for receiving and guiding at least a portion of said each control cable within said tubular portion, each said cable coating having a proximal side; and a threaded sleeve for each cable coating, pivotably mounted in said tubular portion, wherein the proximal side of each said cable coating is attached to a corresponding threaded sleeve.

12. The apparatus of claim 11, wherein each threaded sleeve is mounted at a predetermined position, further comprising means for longitudinally adjusting said predetermined positions of said threaded sleeves to adjust the control cables in a direction of said central endoscope axis.

* * * * *